(12) United States Patent
Boese

(10) Patent No.: US 8,023,616 B2
(45) Date of Patent: Sep. 20, 2011

(54) METHOD AND APPARATUS FOR SETTING A DYNAMICALLY ADJUSTABLE POSITION OF AN IMAGING SYSTEM

(75) Inventor: Jan Boese, Eckental (DE)

(73) Assignee: Siemens Aktiengesellschaft, Munich (DE)

( * ) Notice: Subject to any disclaimer, the term of this patent is extended or adjusted under 35 U.S.C. 154(b) by 4 days.

(21) Appl. No.: 12/501,539

(22) Filed: Jul. 13, 2009

(65) Prior Publication Data

US 2010/0014629 A1    Jan. 21, 2010

(30) Foreign Application Priority Data

Jul. 15, 2008   (DE) .................... 10 2008 033 137

(51) Int. Cl.
*G01N 23/00*  (2006.01)
*H05G 1/62*  (2006.01)

(52) U.S. Cl. ............................................ 378/8; 378/95

(58) Field of Classification Search .............. 378/62–65, 378/68, 69, 95, 97, 108, 165, 4–20
See application file for complete search history.

(56) References Cited

U.S. PATENT DOCUMENTS

2006/0193435 A1 *   8/2006   Hara et al. ...................... 378/65

FOREIGN PATENT DOCUMENTS

| DE | 10210646 A1 | 10/2003 |
|---|---|---|
| DE | 102004048209 B3 | 9/2005 |
| DE | 102005032523 A1 | 1/2007 |
| DE | 102005049106 A1 | 4/2007 |

OTHER PUBLICATIONS

Siemens AG, Medical Solutions, AX; AXIOM Artis / Quick Guide for Special Examinations / Software Version VB30 and higher; Print No. AXA4-300.622.10.01.02 / 05.2006; Others; 2006.
Siemens AG, Medical Solutions, "*syngo* InSpace 3D, DynaCT and DynaCT Cardiac", *syngo* Workplace, Perator Manual, VB13 and higher, Feb. 2008, pp, 1-84, Siemens AG, Medical Solutions Angiography, Fluoroscopic and Radiographic Systems, Order No. AX42-010.621.54.02.02, Germany.

* cited by examiner

*Primary Examiner* — Anastasia Midkiff

(57) ABSTRACT

The invention relates to a method and an apparatus for setting a dynamically adjustable position of an imaging system for providing an optimum view onto a moving object during a medical intervention. A time-resolved at least three-dimensional data record of the moving object is generated. A position of the imaging system for each period of time is determined from the time-resolved data record from which the optimum view onto a structure of interest of the moving object is produced and automatically setting a calculated position of the imaging system in real-time so that the optimum view onto the structure of interest can be shown at any time. Optionally prior to determining the position of the imaging system, a structure of interest of the moving object can be segmented with this structure being segmented for each period of time from the time-resolved data record.

9 Claims, 3 Drawing Sheets

Step 1:
4D image series

Time

Step 2:
Segmented aorta valve ring

Step 3:
Calculate the optimal angulation

RAO 40    RAO 30    RAO 10    RAO 5    RAO 20
CRAN 30   CRAN 20   CRAN 10   CRAN 10  CRAN 20

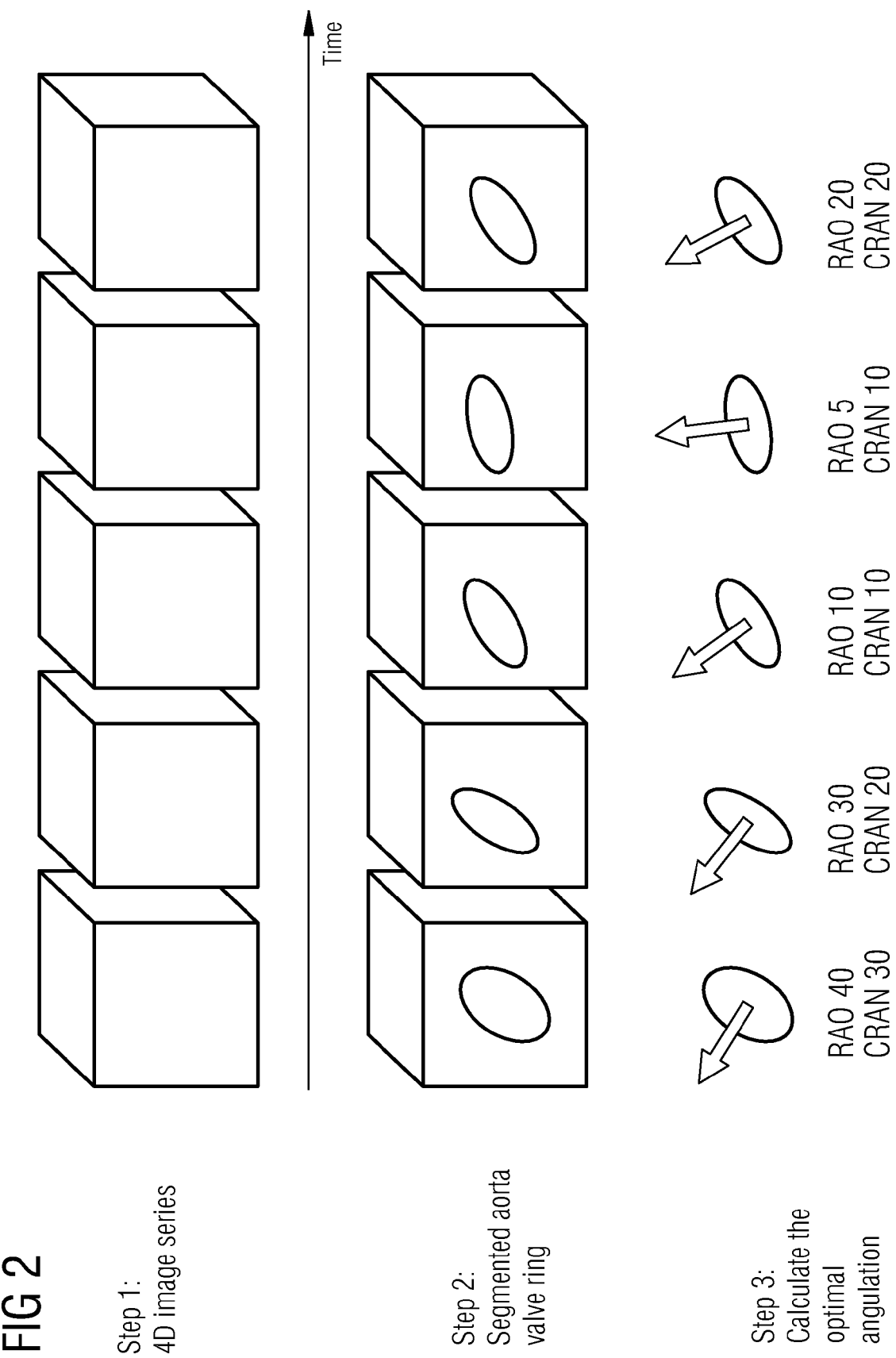

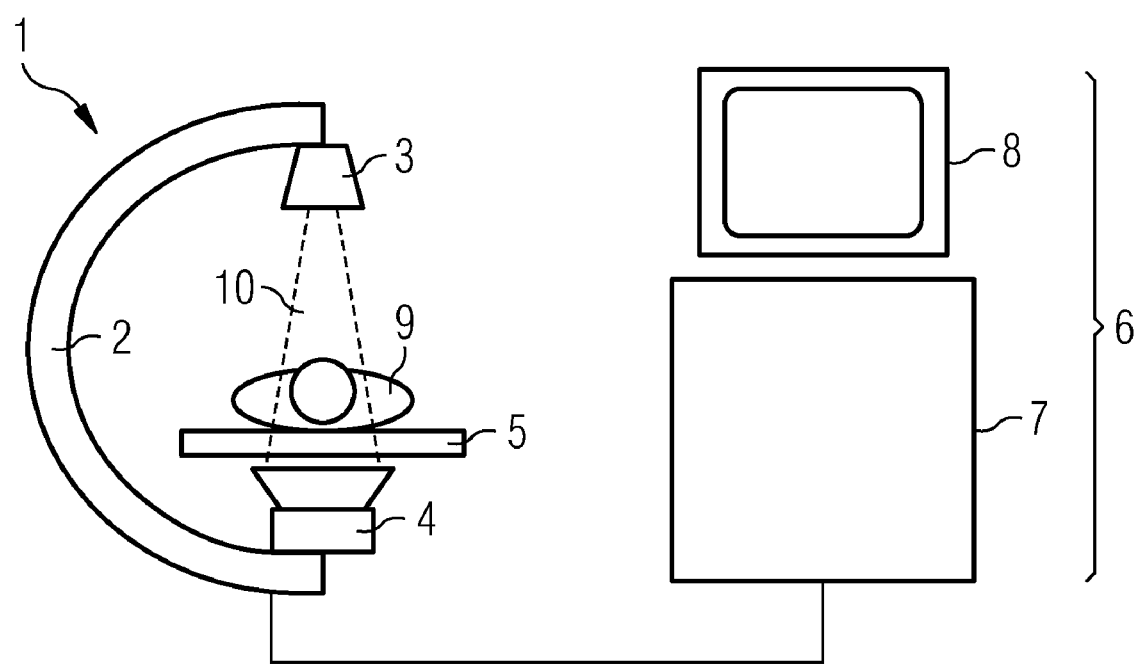

METHOD AND APPARATUS FOR SETTING A DYNAMICALLY ADJUSTABLE POSITION OF AN IMAGING SYSTEM

CROSS REFERENCE TO RELATED APPLICATIONS

This application claims priority of German application No. 10 2008 033 137.6 filed Jul. 15, 2008, which is incorporated by reference herein in its entirety.

FIELD OF THE INVENTION

The invention relates to a method and an apparatus for setting a dynamically adjustable position of an imaging system for providing at least one optimum view onto a moving object preferably during a medical intervention.

BACKGROUND OF THE INVENTION

The invention preferably relates to angiography systems, which are used for interventional operations on the heart for instance. Such angiography systems are generally represented by C-arm x-ray devices. It is possible to generate three-dimensional (3D) or even four-dimensional (4D corresponds to 3D plus time) image data using angiography systems, like is known for instance from DE 10 2004 048 209 B3.

One problem with the use of 3D or 4D volume data during the intervention is the introduction of real-time fluoroscopy images in conjunction with the volume data.

A so-called 2D/3D registration is normally used to solve this problem. The real-time fluoroscopy image is shown in a fused state with a view of the volume data which is suited to the current position of the C-arm, as is known for instance in DE 10210646A1.

The function of the real-time tracking of the 3D view during changes to the C-arm position or the adjustment of the C-arm to a manually selected 3D view is particularly useful here. This is realized for instance in the product AXIOM Artis by the company Siemens with the features "Adjust 3D" and "Adjust C-Arm" ("syngo Workplace Operator Manual VB13 and higher", © Siemens AG, Order no.: AX42-010.621.54.02.02, which can be ordered from Siemens AG, Medical Solutions Angiography, Fluoroscopic and Radiographic Systems Siemensstrasse 1, D-91301 Forchheim, Deutschland, http://www.siemens.com/medical).

The said function is essentially restricted in that it only allows the use of a static 3D data record to set the C-arm at a certain point in time. If a moving object, e.g. a heart, is to be examined and/or operated, the optimum C-arm setting can only be performed for a certain heart phase. 4D data could previously not be used for "Adjust C-Arm".

This method is unfavorable particularly with structures which implement the complex movements, like for instance the aorta valve. To assist with procedures, like for instance the interventional aorta valve replacement, it is expedient if a tracked optimum view of the valve plane is achieved in real-time.

SUMMARY OF THE INVENTION

It is the object of the invention to improve the afore-cited procedure.

This object is achieved by the features specified in the independent claims. Advantageous developments of the invention are specified in the dependent claims.

One essential aspect of the invention, based on time-resolved 3D data, is to determine an optimum C-arm position and/or angulation for each of the individual time phases and to subsequently move the C-arm in real-time into the angulation suited to the current point in time.

The subject matter of the invention is a method for setting a dynamically adjustable position of an imaging system for providing at least one optimum view onto a moving object during a medical intervention, characterized by the following steps:

a) using at least one generated time-resolved, at least three-dimensional data record of the moving object, b) determining a position of the imaging system for each period of time from the time-resolved data record, from which at least an optimum view onto the structure of interest of the moving object results and c) automatically setting a calculated position of the imaging system from step (b) in real time so that an optimum view onto the structure of interest can be shown at any time.

A structure of interest of the moving object can optionally be segmented before step b), with this structure being segmented for each period of time from the time-resolved data record.

Expediently, a C-arm x-ray system can be used as an imaging system and the position and/or angulation of the C-arm can be set in real-time in the afore-described step c).

It is favorable if the C-arm x-ray system includes a robot-controlled C-arm.

The period of times and/or time phases from the time-resolved data record may include phases from the heart and/or breathing movements of the moving object. The structure of interest may in this case be an aorta valve ring. An optimum view onto the aorta valve ring generally results at right angles hereto.

One further aspect of the invention is an apparatus, in particular a C-arm x-ray system, suited to implementing the inventive method, characterized by means for calculating a position of the C-arm for each period of time from a time-resolved data record, from which at least one optimum view onto the structure of interest results and means for automatically setting a calculated position of the C-arm in real-time, so that an optimum view onto the structure of interest can be shown at any time.

A C-arm x-ray system is advantageous, this being characterized by a robot-controlled C-arm.

The invention allows a real-time adjustment of the C-arm angulation and/or position on a structure of interest to the intervention. With the afore-cited example of the heart valve replacement, the C-arm moves in real-time such that despite the heart movement, a right-angled view onto the aorta valve plane is always possible.

The inventive procedure can also be used in other instances in which organ movement plays a role, for instance an adjustment of the C-arm to the breathing movement in the case of interventions in lungs or the abdomen. The inventive procedure can be extended such that account can be easily taken of both the breathing and heart movements (in this case 5D data records are generated). This could increase the accuracy and reliability of the interventional operation, particularly in instances in which a very precise positioning of a heart valve is necessary.

BRIEF DESCRIPTION OF THE DRAWINGS

An exemplary embodiment of the invention is described in more detail below with reference to a drawing, in which:

FIG. 1 shows a schematic representation of a flow chart of the inventive procedure and FIG. 2 shows steps of the inventive procedure.

FIG. 3 shows a C-arm x-ray system for implementing the inventive method,

DETAILED DESCRIPTION OF THE INVENTION

Figure 1:
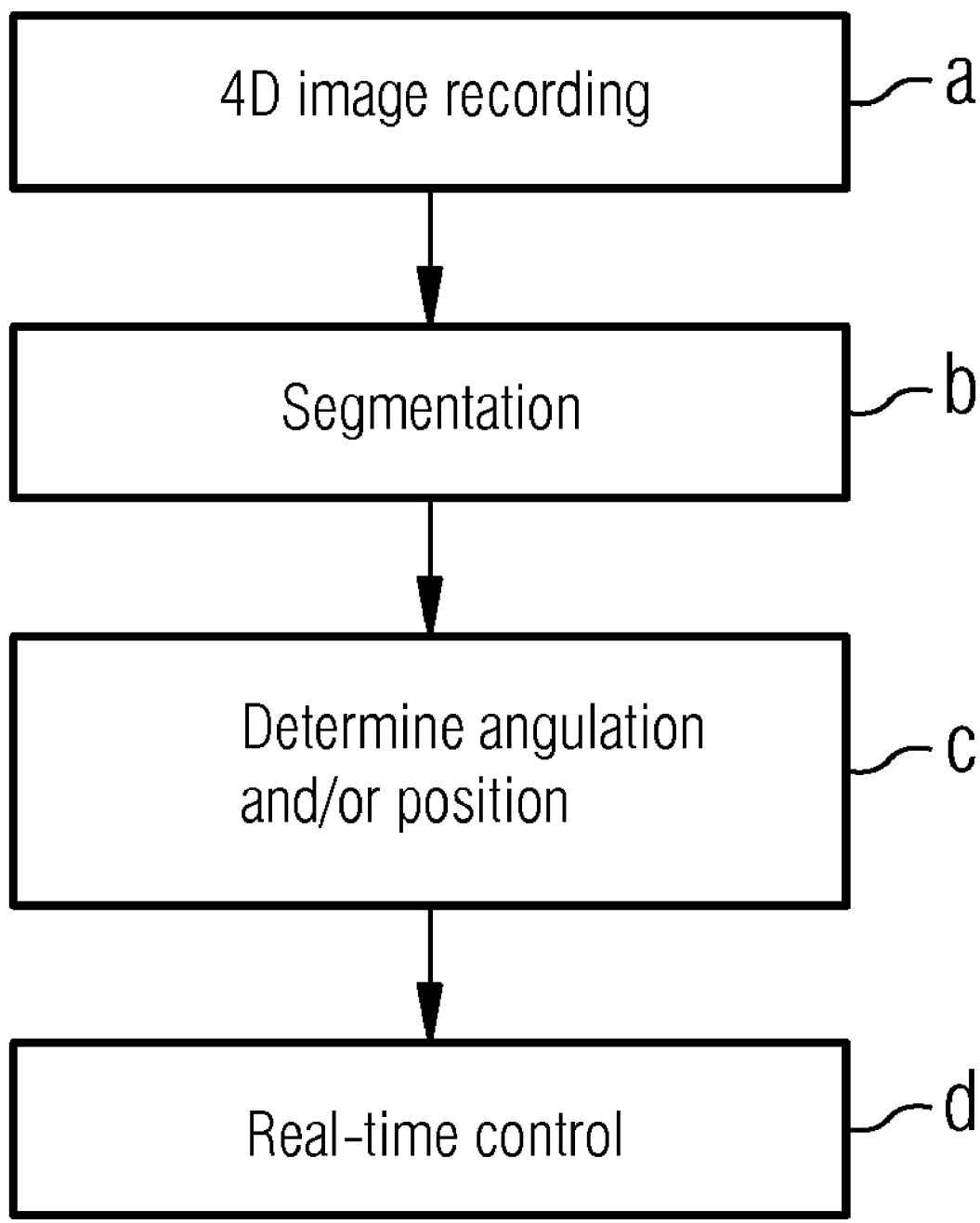

FIG. 3 shows a C-arm x-ray system 1 for instance which has a rotatably mounted C-arm 2, to the ends of which are attached an x-ray radiation source, for instance an x-ray emitter 3 and an x-ray image detector 4. The x-ray image detector 4 may be a rectangular or square flat semi-conductor detector, which is preferably manufactured from amorphous silicon. A patient support table 5 for accommodating a structure of interest, for instance a moving object, e.g. heart or lung of a patient 9, is located in the radiation path of the radiation source 3. An image system 6 is connected to the x-ray system, said image system receiving and processing the image signals of the x-ray detector 4. The image system 6 also includes an evaluation computer 7 and a reproduction apparatus 8, preferably embodied as a dual-monitor System.

The rotatably mounted C-arm 2 comprising x-ray emitter 3 and image detector 4 is rotated in order to generate 3D image data records. The x-ray radiation source 3 imitates a beam bundle 10 based on a beam focus of the x-ray radiation source 3, said beam bundle 10 striking the x-ray image detector 4. The x-ray radiation source 2 and the x-ray image detector 4 pass around the structure of interest in each instance such that the x-ray radiation source 2 and the x-ray image detector 4 are disposed on opposite sides of the structure of interest.

FIG. 1 shows a schematic representation of a flow chart of the inventive procedure.

An ideal condition of the invention is a C-arm which can be moved flexibly and rapidly in real time so that this invention can be particularly well realized on robot-based angiography systems.

The inventive method consists of four steps, which are identified in FIG. 1 with the letters a to d:

a) Image acquisition:
A time-resolved 3D data record, in other words a so-called 4D data record is recorded. The fourth dimension is preferably a time parameter such as a heart phase or breathing phase.

b) Segmentation of a structure, with this step being optional:
A structure of interest is segmented from the recorded 4D data. This is a structure which is relevant to the selection of the optimum C-arm angulation and/or position. The heart valve replacement procedure here may be an aorta valve ring for instance. This structure is segmented for each individual period of time of the volume data so that a 4D model of the structure is obtained as a result.

c) Determination of the optimum C-arm angulation and position:
The optimum C-arm angulation and position is calculated from the 4D model of the structure. An algorithm which is possibly dependent on a clinical problem is used for this purpose, said algorithm ensuring that using the resulting angulation, as optimum a view as possible can be achieved in order to control the interventional steps. In the case of the heart valve replacement procedure, a direction at right angles to the aorta valve ring could be used for instance. This direction would be favorable in order to assess the position of a cap to be used. This calculation is used individually for each period of time of the 4D model, so that a set of angulation directions and/or C-arm positions are obtained as a result.

d) Real-time control of the C-arm:
In the last step, the calculated set of angulation directions is used and the angulation (and/or position) which is suited to the current state is selected. This is transmitted by means of real-time control to the C-arm, so that this moves in real-time with the structure.

The inventive procedure can also be used in other instances, in which organ movement plays a role, e.g. an adjustment of the C-arm to the breathing movement in interventions in lungs or the abdomen is conceivable. The inventive procedure can be extended such that account can also be easily taken of both the breathing and also heart movement (in this case 5D data records are generated). This could increase the precision and reliability of the interventional operation, in particular in instances in which a very precise positioning of a heart valve is needed.

FIG. 2 shows essential steps of the inventive procedure. FIG. 2 shows a time axis. In step 1, comparable with step a from FIG. 1, an already afore-cited 4D image series is generated. In step 2, comparable with step b from FIG. 1, a structure of interest, e.g. an aorta valve ring, is segmented in each image generated at any period of time. In step 3, comparable with step c from FIG. 1, an optimum angulation, e.g. in RAO and/or CRAN (RAO=Right Anterior Oblique, CRAN=Cranial, the two angular positions of a C-arm are thus typically identified in the left/right and/or upper/lower direction; in the example at right angles to the aorta valve ring, which is indicated in the Figure with an arrow) is calculated at each period of time) and a C-arm arm position is determined therefrom.

The invention is not restricted to the afore-cited embodiments. Further variations of the invention are conceivable. Within the scope of the invention, an imaging system preferably comprises x-ray C-arm systems, x-ray biplane devices, computed tomographs, magnetic resonance or PET devices. In the case of C-arm devices, the C-arm can also be replaced by a so-called electronic C-arm, in which an electronic coupling of the x-ray emitter and x-ray image detector takes place. The C-arm can also be guided on robot arms, which are attached to the ceiling or floor. The invention can also be implemented with x-ray devices, in which imaging devices are held in each instance by a robot arm, which are arranged on the ceiling and/or floor of the examination room and/or operating theatre.

The invention claimed is:

1. A method for setting a position of an imaging system to provide an optimum view based on an orientation of a structure of interest of a moving object during a medical intervention, comprising:
   generating a time-resolved three-dimensional data record of the moving object;
   determining a position of the imaging system for each period of time from the time-resolved data record to provide the optimum view of the structure of interest of the moving object;
   automatically setting the position of the imaging system to maintain the same optimum view as the object moves; and
   displaying the optimum view of the structure of interest in real time.

2. The method as claimed in claim 1, further comprising segmenting the structure of interest of the moving object for the each period of time prior to determining the position of the imaging system.

3. The method as claimed in claim 1, wherein the imaging system is a C-arm x-ray system and the position of the C-arm x-ray system is set in real-time.

4. The method as claimed in claim 3, wherein the C-arm x-ray system comprises a robot-controlled C-arm.

5. The method as claimed in claim 1, wherein the each period of time comprises a phase from a heart or a breathing movement of the moving object.

6. The method as claimed in claim 1, wherein the structure of interest is an aorta valve ring and the optimum view of the aorta valve ring is produced at a right angle relative to an aorta valve plane.

7. The method as claimed in claim 1, wherein the position of the imaging system is dynamically determined and adjusted in real time.

8. A C-arm x-ray system, comprising:
a C-arm;
an x-ray radiation source;
an x-ray image detector that records a time-resolved three-dimensional data record of a moving object;
an evaluating computer that determines a position of the C-arm for each period of time from the time-resolved data record to provide an optimum view based on an orientation of a structure of interest of the moving object;
a device that automatically sets the position of the C-arm; and
a display device that displays the same optimum view of the structure of interest in real time.

9. The C-arm x-ray system as claimed in claim 8, wherein the C-arm is a robot-controlled C-arm.

* * * * *